(12) United States Patent  
Claes et al.

(10) Patent No.: US 6,428,540 B1  
(45) Date of Patent: Aug. 6, 2002

(54) DEVICE FOR REPOSITIONING FRACTURED BONE FRAGMENTS

(75) Inventors: Lutz Claes, Neu-Ulm; Heinz Gerngross, Ulm; Götz Rübsaamen, Traunstein, all of (DE); Orlando Martinelli, Bern; Erwin Flühler, Allschwil, both of (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/473,118

(22) Filed: Dec. 28, 1999

Related U.S. Application Data

(63) Continuation of application No. 09/308,288, filed on May 12, 1999, which is a continuation of application No. PCT/CH97/00406, filed on Oct. 27, 1997.

(30) Foreign Application Priority Data

Nov. 13, 1996 (DE) ..................... 296 19 711 U

(51) Int. Cl.[7] .................................................. A61F 5/04
(52) U.S. Cl. ........................................................ 606/53
(58) Field of Search ............................. 606/53, 54, 57, 606/58, 59, 105

(56) References Cited

U.S. PATENT DOCUMENTS

| | | | |
|---|---|---|---|
| 1,997,466 A | 4/1935 | Longfellow | 128/92 |
| 2,238,869 A | 4/1941 | Haynes | 128/92 |
| 2,238,870 A | 4/1941 | Haynes | 128/92 |
| 2,250,417 A | 7/1941 | Ettinger | 128/92 |
| 2,251,209 A | 7/1941 | Stader | 128/92 |
| 2,333,033 A | 10/1943 | Mraz | 128/92 |
| 2,391,537 A | 12/1945 | Anderson | 128/84 |
| 2,391,693 A | 12/1945 | Ettinger | 128/84 |
| 2,393,694 A | * 1/1946 | Kirschner | 606/59 |
| 4,365,624 A | * 12/1982 | Jaquet | 128/92 A |
| 4,488,542 A | 12/1984 | Helland | 128/92 A |
| 4,548,199 A | 10/1985 | Agee | 128/92 |
| 4,554,915 A | 11/1985 | Brumfield | 128/92 |
| 4,628,919 A | 12/1986 | Clyburn | 128/92 |
| 4,628,922 A | * 12/1986 | Dewar | 128/92 |
| 4,662,365 A | 5/1987 | Gotzen et al. | 128/92 |
| 4,696,293 A | 9/1987 | Ciullo | 128/92 |
| 4,730,608 A | 3/1988 | Schlein | 128/92 |
| 4,782,842 A | 11/1988 | Fietti, Jr. | 128/92 |
| 4,919,119 A | 4/1990 | Jonsson et al. | 606/54 |
| 4,922,896 A | 5/1990 | Agee et al. | 606/55 |
| 4,978,348 A | 12/1990 | Ilizarov | 606/57 |
| 4,988,349 A | 1/1991 | Pennig | 606/58 |
| 5,041,112 A | 8/1991 | Mingozzi et al. | 606/54 |
| 5,062,844 A | 11/1991 | Jamison et al. | 606/54 |
| 5,122,140 A | 6/1992 | Asche et al. | 606/55 |
| 5,203,783 A | 4/1993 | Härle | 606/53 |
| 5,275,599 A | 1/1994 | Zbikowski et al. | 606/54 |
| 5,304,177 A | 4/1994 | Pennig | 606/58 |
| 5,314,426 A | 5/1994 | Pohl et al. | 606/58 |
| 5,320,622 A | 6/1994 | Faccioli et al. | 606/58 |
| 5,358,504 A | 10/1994 | Paley et al. | 606/56 |
| 5,376,091 A | 12/1994 | Hotchkiss et al. | 606/55 |

(List continued on next page.)

FOREIGN PATENT DOCUMENTS

| | | |
|---|---|---|
| EP | 0 457 017 A1 | 11/1991 |
| EP | 0 784 962 A1 | 7/1997 |
| GB | 2095999 | 10/1982 |
| GB | 2110094 | 6/1983 |
| WO | WO 92/02184 | 2/1992 |

*Primary Examiner*—Todd E. Manahan  
*Assistant Examiner*—David C. Comstock  
(74) *Attorney, Agent, or Firm*—Pennie & Edmonds LLP

(57) ABSTRACT

A device for repositioning fractured bone fragments has a rod and a clamping device secured to each end of the rod and bone fasteners for anchoring in the fractured bone fragments to be fixed. The rod has three translation mechanisms and three rotation mechanisms for altering the relative position of the two clamping devices so that the device has in total 6 degrees of freedom along the axes $T_x$, $T_y$, $T_z$, $R_x$, $R_y$, and $R_z$.

18 Claims, 2 Drawing Sheets

U.S. PATENT DOCUMENTS

| | | | |
|---|---|---|---|
| 5,397,322 A | * 3/1995 | Campopiano | 606/57 |
| RE34,985 E | 6/1995 | Pennig | 606/58 |
| 5,437,666 A | * 8/1995 | Tepic et al. | 606/55 |
| 5,437,667 A | 8/1995 | Papierski et al. | 606/55 |
| 5,454,810 A | 10/1995 | Pohl et al. | 606/59 |
| 5,545,162 A | 8/1996 | Huebner | 606/57 |
| 5,591,164 A | 1/1997 | Nazre et al. | 606/59 |
| 5,601,551 A | * 2/1997 | Taylor et al. | 606/54 |
| 5,658,283 A | 8/1997 | Huebner | 606/57 |
| 5,662,649 A | 9/1997 | Huebner | 606/57 |
| 5,662,650 A | 9/1997 | Bailey et al. | 606/59 |
| 5,707,370 A | 1/1998 | Berki et al. | 606/59 |
| 5,709,681 A | 1/1998 | Pennig | 606/54 |
| 5,743,898 A | 4/1998 | Bailey et al. | 606/54 |
| 6,109,769 A | * 2/2000 | McCarthy et al. | 606/105 |

* cited by examiner

DEVICE FOR REPOSITIONING FRACTURED BONE FRAGMENTS

CROSS REFERENCE TO RELATED APPLICATIONS

This application is a continuation of application Ser. No. 09/308,288, filed May 12, 1999 which is the U.S. national stage of International Patent Application PCT/CH97/00406 filed Oct. 27, 1997, the content of which is expressly incorporated herein by reference thereto.

FIELD OF THE INVENTION

This invention relates to a system for resetting bone-fracture fragments.

BACKGROUND OF THE INVENTION

A number of devices for the alignment or realignment of the fragments of a fractured bone are known in the art. For example, WO 95/24161 discloses a repositioning device for gradual correction of a bone fracture that has been set in the operating room and is attached to an external fixation device. The disclosed device is limited to acting in three directions and is adjustable only along a single plane. Repositioning of this device involves the following steps:

The repositioning unit is attached to the fixation unit in such manner that the center of rotation of the repositioning unit is lined up with the fracture. The rotational and translational repositioning is performed in a first plane whereupon the joints of the fixation unit are locked in position, stabilizing the fracture.

Next, the screws connecting the repositioning unit and the fixation unit are loosened and the entire repositioning unit is swiveled into a second plane which is preferably perpendicular to the first plane, followed by a retightening of the connecting screws. The joints of the fixation unit are unlocked, the unit is repositioned in the second plane and the joints are again locked in position.

The drawback of this concept lies in the fact that for rotational repositioning around the longitudinal axis of the bone, an articulated parallelogram must be mounted between the fixation unit and the repositioning unit, involving corresponding efforts and complexities.

SUMMARY OF THE INVENTION

The following invention is designed to solve the problem. It is based on a concept intended to permit all repositioning steps to be performed quickly and dependably.

The present invention relates to a device for repositioning fragments of a fractured bone. The device includes a first clamping unit attached to the bone by at least one first bone fastener, a second clamping unit attached to the bone by at least one second bone fastener, first, second, and third translation components operatively associated with at least one of the first and second clamping unit for relative translational movement of one clamping unit with respect to the other along a respective first, second, and third translation axis, and first, second, and third rotation components operatively associated with at least one of the first and second clamping unit for relative rotational movement of one clamping unit with respect to the other about a respective first, second, and third rotation axis.

Preferably, each of the translation and rotation components can be operated independently of the others. In one embodiment, the first, second, and third translation axes form an oblique-angle coordinate system.

The device can also include first and second parallel rod sections. The first and second clamping units each comprises a clamping jaw for receiving the bone fasteners and a connecting jaw connecting the clamping jaw to the first and second rod sections. The first rod section connects the first clamping unit to the first rotation component, and the first rotation component comprises a curved bar member, with the first rod section movable along the curved bar member while still maintaining a parallel relationship between the first and second rod sections. Preferably, the curved bar member has a radius of about 50 to 200 mm. The second rod section connects the second clamping unit to the second rotation component and operation of the second rotation component pivots the second rod section about the second rotation axis. The second and third translation components and the third rotation component are each connected to the first rod section. Additionally, the second rotation component engages the third rotation component to connect the first and second clamping units.

The first rotation component preferably has a receiving component having a channel for slidably receiving the curved bar member and an adjustment mechanism for causing movement of the curved bar member relative to the receiving component. The first translation component preferably comprises a tubular cylinder configured for slidably receiving a first end of the first rod section and an adjustment mechanism for causing relative movement of the first rod section and tubular cylinder.

The second and third translation components each preferably comprises a first block having a slotted track and fixed to the third translation component, a second block, at least a portion of which is slidably received in the slotted track, and a drive for causing relative movement between the first and second blocks. The second and third rotation components each preferably comprises a mount having a U-shaped slot at one end, a pivoting element, at least a portion of which is received in the slot, a pin pivotably coupling the mount and the pivoting element; and a drive for causing pivoting of the pivoting element with respect to the mount.

Its advantage is based on the ability to permit repositioning around the longitudinal axis of the bone by means of a progressively rotatable segmental arch, a concept which eliminates time-consuming setup operations.

The chief benefits of this invention are offered by the fact that the system according to this invention permits rapid resetting of the bone fragments without the complicated flip-over into two different planes (an iterative process in prior art).

BRIEF DESCRIPTION OF THE DRAWINGS

This invention and enhanced embodiments thereof are described below in more detail with the aid of partially schematic illustrations of several implementation examples. In the diagrams.

DETAILED DESCRIPTION OF THE PREFERRED EMBODIMENTS

Figure 1:
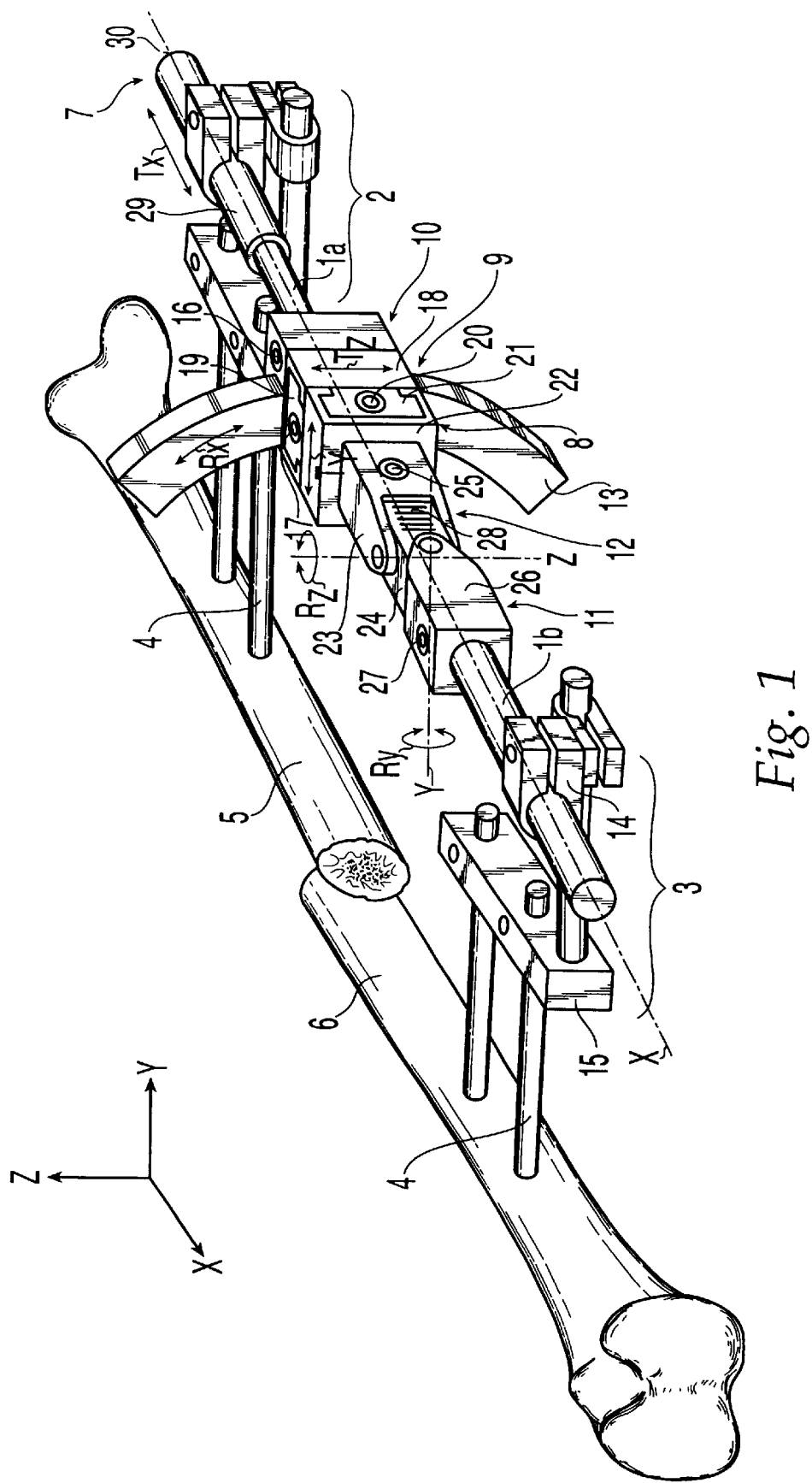
FIG. 1 is a perspective view of the system according to this invention.
Figure 2:
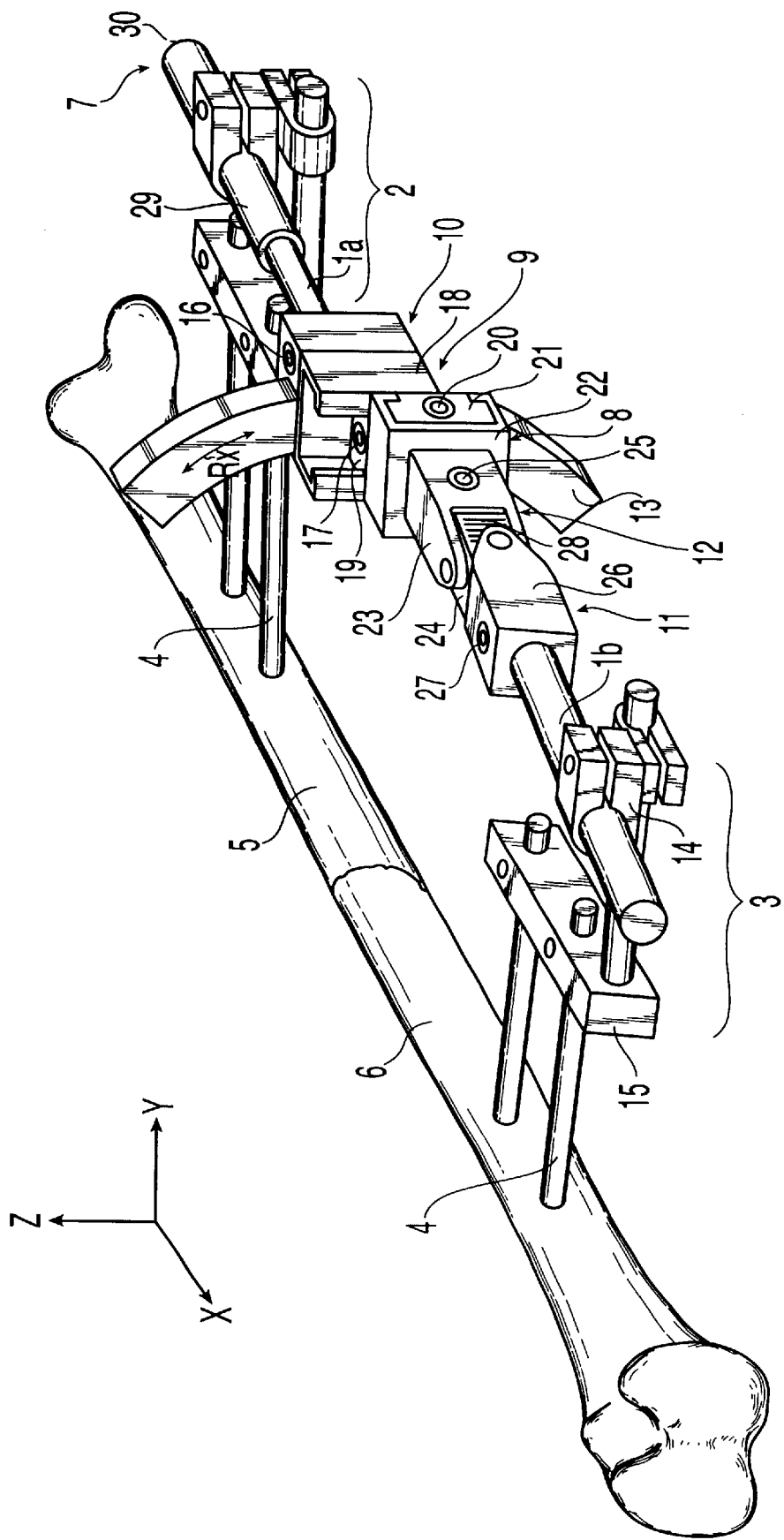
FIG. 2 is a perspective view of the system of FIG. 1 following its translatory movement in the $T_z$ direction and rotation around the axes $R_y$ and $R_z$.

The disclosed system shown in FIG. 1 and 2 for the resetting of bone-fracture fragments essentially consists of a rod 1a, 1b, extending in the x-direction, at the ends of which a clamping device 2 and 3, respectively, can be attached. Both devices 2 and 3 consist of a connecting jaw 14 and a clamping jaw 15 which can accommodate a number of bone fasteners 4, i.e. Schanz screws, for insertion in the bone-fracture fragments 5, 6 that are to be fastened.

The rod incorporates three translatory components 7, 8, 9 and three rotary components 10, 11, 12 which components permit relative positional changes of the two clamping devices 2, 3 with freedom of movement in a total of six directions along the axes $T_x, T_y, T_z, R_x, R_y, R_z$, with the axes $T_x, T_y$ and $T_z$ of the translatory components 7, 8, 9 establishing a rectangular coordinate system. An oblique-angled coordinate system would also be possible provided the data collected can be acquired and processed by a computer.

The rod is made up of two separate sections 1a, 1b of which, by means of the rotary component 10, the rod section 1a can be shifted around a circular arc segment 13 located in the y,z-plane, while still maintaining its parallel relationship with the other rod section 1b. The circular arc segment 13 is rotatably bearing-mounted, via the adjustment mechanism 16, in the square-block-shaped rotary component 10. The rod section 1a is laterally attached, in fixed position, to the circular arc segment 13 so that any rotation of the adjustment mechanism 16 causes the rod section 1a to move in unison with the arc section 13 relative to the rotary component 10 along the path defined by the arc segment 13. The circular arc segment 13 has a radius of between 50 and 200 mm and preferably between 80 and 130 mm. The larger the radius of the arc segment, the greater the distance at which the repositioning unit can be mounted from the longitudinal axis of the bone. However, the size of the radius is limited if conventional Schanz screws are used as bone fasteners 4.

The translatory component 7 for the x-axis consists of both the rod section 1a and a tubular cylinder 29 inside which the rod section 1a is positioned. The rod section 1a and the tubular cylinder 29 can be moved in relation to each other along the x-axis by means of an adjustment device 30 for instance in the form of a lead-screw drive.

The positional sequence of the translatory components 7, 8, 9 and the rotary components 10,11,12 in the x-direction corresponds to the sequence $T_x, R_x, T_z, T_y, R_z, R_y$.

In the embodiment illustrated in FIG. 1, the translatory components 8, 9 for the $T_y, T_z$, axes and the rotary component 10 for the $R_x$ axis are combined into one unit; however, they may equally well be designed as individual elements or they may be combined in pairs.

The translatory component 9 for the z-axis consists of two square blocks which can be moved relative to each other in the z- direction by a drive 17; the block segment 18 is connected, in fixed position, to the rotary component 10 and is provided with a slotted track in which the other block segment 19, operating as a slide, can be moved by the drive 17.

The translatory component 8 for the y-axis on its part consists of two square blocks which can be moved relative to each other by a drive 20; one block segment 21, operating as a slide, is solidly connected to the sliding block segment 19 of the translatory component 9 and can be moved in the slotted track of the other block segment 22 by the drive 20.

The block segment 22 of the translatory component 8 is solidly connected to the rotary component 12, the latter consisting of two mutually swivel-connected elements 23, 24 which by means of an adjustment mechanism 25 can be rotated relative to each other around the $R_z$ axis of rotation. The swivel element 23 is solidly connected to the block segment 22 of the translatory component 8 while the other swivel element 24 is connected to the rotary component 11.

The rotary component 11 as well consists of two mutually swivel-connected elements one of which is the swivel element 24 of the rotary component 12 while the other element 26 is solidly connected to rod section 1b. The two swivel elements 24 and 26 are rotatable relative to each other, around the $R_y$ axis of rotation, by means of an adjustment mechanism 27.

For its intended function the swivel element 24 consists of two semicircular arch segments, twisted at a 90° angle relative to each other and each provided with a gear rim 28. The gear drive units 25 and 27 in the form of worm gears engage in the respective gear rims 28, thus providing the ability to move the swivel-type rotary components 11 and 12 around the $R_y$ and $R_z$ axes.

After a completed translatory movement in the $T_z$ direction and rotation around the $R_y$ and $R_z$ axes the system according to this invention will have transitioned from its state per FIG. 1 to that per FIG. 2.

The following describes an example of the operating procedure employing the repositioning system in conjunction with a Fixateur Externe.

EXAMPLE

A) Both fracture fragments are provided with 2 Schanz screws each, later to be connected to each one standard jaw of the fixation unit.

B) By means of two jaw adapters the repositioning unit is connected to the standard jaws. This assembly process is the starting point for the following repositioning procedure. As step 1, an angular correction is performed on the fracture.

C) Any translative deviations are adjusted by a translative correction procedure. Any deviations in the other two planes are corrected as described above (item B). Upon completion of the procedure the fracture is fully corrected in every direction. A longitudinal rod can now be introduced through the two standard jaws and fastened, thus stabilizing the fracture.

D) The two jaw adapters are then separated from the fixation unit. The latter remains with the patient until the fracture is fully healed.

In lieu of its combination with a Fixateur Externe, the system according to this invention can also be used for the angularly stable plating of bone fractures or for inserting marker nails. For angularly stable plating the use of noninvasive bone clamps (per EP 457.017) instead of Schanz screws has been found to be more desirable.

What is claimed is:

1. A device for repositioning fragments of a fractured bone comprising:

a first clamping unit adapted for attachment to the bone by at least one first bone fastener;

a second clamping unit adapted for attachment to the bone by at least one second bone fastener;

a first translation component operatively associated with at least one of the first and second clamping unit for relative translational movement of one clamping unit with respect to the other along a first translation axis;

a first rotation component operatively associated with at least one of the first and second clamping unit for relative rotational movement of one clamping unit with respect to the other about a first rotation axis;

a second translation component operatively associated with at least one of the first and second clamping unit for relative translational movement of one clamping unit with respect to the other along a second translation axis;

a second rotation component operatively associated with at least one of the first and second clamping unit for relative rotational movement of one clamping unit with respect to the other about a second rotation axis;

a third translation component operatively associated with at least one of the first and second clamping unit for relative translational movement of one clamping unit with respect to the other along a third translation axis; and a third rotation component operatively associated with at least one of the first and second clamping unit for relative rotational movement of one clamping unit with respect to the other about a third rotation axis, wherein each of the translation and rotation components can be operated independently of the others.

2. The device of claim 1 wherein the first, second, and third translation axes form an oblique-angle coordinate system.

3. The device of claim 1 further comprising first and second parallel rod sections, the first rod section connecting the first clamping unit to the first rotation component, and wherein the first rotation component comprises a curved bar member, and the first rod section can be moved along the curved bar member while still maintaining a parallel relationship between the first and second rod sections.

4. The device of claim 3 wherein the second rod section connects the second clamping unit to the second rotation component, wherein operation of the second rotation component pivots the second rod section about the second rotation axis.

5. The device of claim 4 wherein the second and third translation components and the third rotation component are each connected to the first rod section.

6. The device of claim 5 wherein the second rotation component engages the third rotation component to connect the first and second clamping units.

7. The device of claim 3 wherein the curved bar member has a radius of about 50 to 200 mm.

8. The device of claim 3 wherein the curved bar member has a radius of about 80 to 130 mm.

9. The device of claim 3 wherein the first rotation component further comprises a receiving component having a channel for slidably receiving the curved bar member; and an adjustment mechanism for causing movement of the curved bar member relative to the receiving component.

10. The device of claim 3 wherein the first translation component comprises a tubular cylinder configured for slidably receiving a first end of the first rod section; and an adjustment mechanism for causing relative movement of the first rod section and tubular cylinder.

11. The device of claim 3 wherein the first and second clamping units each comprises a clamping jaw for receiving the respective at least one first and second bone fastener; and a connecting jaw connecting the respective clamping jaw to the respective first and second rod sections.

12. The device of claim 1 wherein the second and third translation components are provided as a single unit.

13. The device of claim 1 wherein the second and third translation components and the first rotation component are provided as a single unit.

14. The device of claim 1 wherein the third translation component comprises:

a first block having a slotted track and fixed to the first rotation component;

a second block, at least a portion of which is slidably received in the slotted track; and a drive for causing relative movement between the first and second blocks.

15. The device of claim 1 wherein the second translation component comprises:

a first block having a slotted track and fixed to the third translation component;

a second block, at least a portion of which is slidably received in the slotted track; and a drive for causing relative movement between the first and second blocks.

16. The device of claim 1 wherein the third rotation component comprises:

a mount having a U-shaped slot at one end;

a pivoting element, at least a portion of which is received in the slot;

a pin pivotably coupling the mount and the pivoting element; and a drive for causing pivoting of the pivoting element with respect to the mount.

17. The device of claim 1 wherein the second rotation component comprises:

a mount having a U-shaped slot at one end;

a pivoting element, at least a portion of which is received in the slot;

a pin pivotably coupling the mount and the pivoting element; and a drive for causing pivoting of the pivoting element with respect to the mount.

18. A device for repositioning fragments of a fractured bone comprising:

a first clamping unit adapted for attachment to the bone by at least one first bone fastener;

a second clamping unit adapted for attachment to the bone by at least one second bone fastener;

a first translation component operatively associated with at least one of the first and second clamping unit for relative translational movement of one clamping unit with respect to the other along a first translation axis;

a first rotation component operatively associated with at least one of the first and second clamping unit for relative rotational movement of one clamping unit with respect to the other about a first rotation axis;

a second translation component operatively associated with at least one of the first and second clamping unit for relative translational movement of one clamping unit with respect to the other along a second translation axis;

a second rotation component operatively associated with at least one of the first and second clamping unit for relative rotational movement of one clamping unit with respect to the other about a second rotation axis;

a third translation component operatively associated with at least one of the first and second clamping unit for relative translational movement of one clamping unit with respect to the other along a third translation axis; and a third rotation component operatively associated with at least one of the first and second clamping unit for relative rotational movement of one clamping unit with respect to the other about a third rotation axis, wherein the second rotation component engages the third rotation component to connect the first and second clamping units.

* * * * *